(12) United States Patent
Bradley et al.

(10) Patent No.: US 6,894,359 B2
(45) Date of Patent: May 17, 2005

(54) SENSITIVITY CONTROL FOR NANOTUBE SENSORS

(75) Inventors: Keith Bradley, Oakland, CA (US); Philip G. Collins, Irvine, CA (US); Jean-Christophe P. Gabriel, Pinole, CA (US); George Gruner, Los Angeles, CA (US); Alexander Star, Albany, CA (US)

(73) Assignee: Nanomix, Inc., Emeryville, CA (US)

( * ) Notice: Subject to any disclaimer, the term of this patent is extended or adjusted under 35 U.S.C. 154(b) by 160 days.

(21) Appl. No.: 10/280,265

(22) Filed: Oct. 26, 2002

(65) Prior Publication Data

US 2004/0043527 A1 Mar. 4, 2004

Related U.S. Application Data

(60) Provisional application No. 60/408,412, filed on Sep. 4, 2002.
(51) Int. Cl.[7] .......................... H01L 27/14; H01L 29/82; H01L 29/84
(52) U.S. Cl. .......................... 257/414; 257/253; 257/53; 977/DIG. 1
(58) Field of Search ................................ 257/414, 253, 257/53, 798; 977/DIG. 1

(56) References Cited

U.S. PATENT DOCUMENTS

| | | | |
|---|---|---|---|
| 2002/0117659 A1 | 8/2002 | Lieber ........................... | 257/14 |
| 2003/0134433 A1 * | 7/2003 | Gabriel et al. .............. | 436/518 |

FOREIGN PATENT DOCUMENTS

| | | | | |
|---|---|---|---|---|
| WO | WO 01/44796 | 6/2001 | .......... | G01N/27/12 |
| WO | WO 02/48701 | 6/2002 | .......... | G01N/27/00 |

OTHER PUBLICATIONS

Avouris, Ph.; "Molecular electronics with carbon nanotubes," Accounts of Chemical Research, ASAP Article 10.1021/ar010152e S0001–4842(01)00152–2 Web Release Date: Jul. 31, 2002.

Appelzeller, J;, Martel, R.; Avouris, Ph.; "Optimized contact configuration for the study of transport phenomena in ropes of single–wall carbon nanotubes," Appl. Phys. Lett. 78, 3313, (2001).

Collins, P.G.; Bradley, K.; Ishigami, M.; Zettl, A.; "Extreme oxygen sensitivity of electronic properties of carbon nanotubes," Science 287, 1801 (2000).

(Continued)

*Primary Examiner*—Craig A. Thompson
(74) *Attorney, Agent, or Firm*—Nanomix, Inc.; Robert F. Dennis

(57) ABSTRACT

Nanostructure sensing devices for detecting an analyte are described. The devices include nanostructures connected to conductive elements, all on a substrate. Contact regions adjacent to points of contact between the nanostructures and the conductive elements are given special treatment. The proportion of nanostructure surface area within contact regions can be maximized to effect sensing at very low analyte concentrations. The contact regions can be passivated in an effort to prevent interaction between the environment and the contact regions for sensing at higher analyte concentrations and for reducing cross-sensing. Both contact regions and at least some portion of the nanostructures can be covered with a material that is at least partially permeable to the analyte of interest and impermeable to some other species to tune selectivity and sensitivity of the nanostructure sensing device.

39 Claims, 12 Drawing Sheets

OTHER PUBLICATIONS

Cui, J.B.; Burghard, M.; Kern, K.; "Room temperature single electron transistor by local chemical modification of carbon nanotubes," Nano Letters 2, 117(2002).

Derycke, V.; Martel, R.; Appenzeller, J.; Avouris, Ph.; "Carbon nanotube inter—and intramolecular logic gates," Nano Letters 9, 453 (2001).

Derycke, V.; Martel, R.; Appenzeller, J.; Avouris, Ph.; "Controlling doping and carrier injection in carbon nanotube transistors, " Appl. Phys. Lett. 80, 2773 (2002).

Heinze, S.; Tersoff, J.; Martel, R.; Derycke, V.; Appenzeller, J.; Avouris, Ph.; "Carbon nanotubes as Schottky barrier Transistors," Phys. Rev. Lett. 89, 106801 (2002).

Kong, J.; Franklin, N.R.; Zhou, C.; Chapline, M.G.; Peng, S.; Cho, K.; Dai, H.; Science, 287, 622 (2000).

Martel, R.; Derycke, V.; Lavoie, C.; Appenzeller, J.; Chan, K.K.; Tersoff, J.; Avouris, Ph., Phys. Rev. Lett. 87, 256805 (2001).

* cited by examiner

SENSITIVITY CONTROL FOR NANOTUBE SENSORS

DOMESTIC PRIORITY CLAIM

This application claims priority to U.S. Provisional Application No. 60/408,412, filed Sep. 4, 2002.

BACKGROUND OF THE INVENTION

1. Field of the Invention

The invention is directed generally to nanotube sensors and in particular to nanotube sensors with selective passivation of nanotube-conductor contacts and the nanotubes themselves and methods of forming same.

2. Description of the Related Art

Chemical and biological sensors that use nanotube circuits have been reported in the literature. In general, these sensors include a nanotube or nanotubes in contact with electrodes, thus forming a circuit for current flow. It is generally believed that sensing occurs when analytes interact with the exposed nanotube.

Dai et al. (PCT Publication No. WO 01/44796 A1) described a nanotube sensing device which had nanotubes grown from catalyst islands and metal electrodes that covered fully the catalyst islands. The ends of the nanotubes were embedded in the catalyst islands within the metal electrodes.

Lieber et al. (PCT Publication No WO 02/48701 A2) described a nanowire sensing device that was particularly adapted for sensing analytes in fluids delivered through a microchannel to the nanowire which was connected to two metal electrodes.

Nanotube sensors have been reported to respond to chemical species such as ammonia (Kong, J., et al., *Science*, 287, 622 (2000)). These sensors exhibited a fast response and a substantially slower recovery. Other researchers have found that nanotube sensors are unpredictable in their response to ammonia. For some sensors the resistance went up in response to the analyte, for some it went down, and the magnitude of the response was variable as well. The sensors had both nanotubes and electrode/nanotube contacts that were exposed to the surrounding atmosphere.

In semiconductor device technology, it is well known that metal contacts to silicon can be sensitive and problematic. Schottky barriers at metal/semiconductor junctions create a large number of surface states that are very sensitive to the surrounding environment. For this reason, among others, metal/semiconductor contacts have been passivated by covering the device with a layer of insulating material. Thus the contacts do not come into contact with the surrounding environment, nor is any other part of the device exposed to the surrounding environment.

Scientists at IBM have conducted research on nanotube transistor devices that were configured to act as electronic devices, not as sensing devices. Nanotube device characteristics changed depending on their exposure to oxygen. As-made devices generally exhibited p-type transistor characteristics. Derycke, et al. (Appl. Phys. Lett. 80, 2773 (2002)) reported that their devices changed to n-type transistors after heating in vacuum. The change could be reversed only be exposing the devices to oxygen. They attributed this behavior to removal of adsorbed oxygen from the contacts. Their key finding was that the main effect of oxygen adsorption was to modify the barriers at the metal-semiconductor contacts.

Avouris has reported (Accounts of Chemical Research, ASAP Article 10.1021/ar010152e S0001-4842(01)00152-2 Web Release Date: Jul. 31, 2002.) enclosing p-type carbon nanotube field effect transistors in $SiO_2$ and annealing them at 700° C. in an inert gas or in vacuum. Subsequent electrical measurements showed that the devices had become ambipolar (with conduction by either holes or electrons) transistors. The ambipolar behavior was observed only when the device was passivated by a film of $SiO_2$ before the thermal annealing. At the high annealing temperature, $O_2$ can diffuse through the oxide and desorb. Upon cooling, however, the $SiO_2$ film protects the device from oxygen. Avouris concluded that the observed electrical behavior was dominated by oxygen's effect on the Schottky barriers at the metal-nanotube junctions.

Nanostructure sensing devices are most often used to detect a species of interest in a surrounding environment. Electrical signals from the nanostructure sensing devices can be measured before and after exposure to the environment. Changes in measured signals can be correlated to detection of a species. Total passivation of a nanostructure sensing device could result in gross underreporting of detection events if the species of interest cannot diffuse through the passivation layer and reach the nanostructure sensing device. On the other hand, very sensitive Schottky barriers may respond to species that are not of interest, such as moisture or oxygen. Large electrical responses from Schottky barriers could overwhelm smaller nanostructure responses from detection of species of interest.

It would be useful to understand better analyte interactions at Schottky barriers and at nanostructures. This understanding could be used to design nanostructure sensing devices in various configurations to exploit the special sensing characteristics of both Schottky barriers and nanostructures in nanostructure sensing devices.

SUMMARY OF THE INVENTION

In accordance with one aspect of the present invention an electronic system for detecting analytes is provided. The system includes a signal control and processing unit in communication with at least one nanostructure sensing device. The nanostructure sensing device circuit comprises an electrical supply, a meter and a nanostructure sensing device connected together in the circuit. The nanostructure sensing device comprises at least one nanostructure connected to at least two conductive elements, all disposed over a substrate. There are contact regions adjacent to the connections between the conductive elements and the nanostructure, and inhibiting material covering at least the contact regions. In one arrangement, the electronic system includes functionalization of at least one nanostructure sensing device. In another arrangement, the functionalization for a first nanostructure sensing device is different from the functionalization for a second nanostructure sensing device.

In accordance with another aspect of the invention a nanostructure sensing device for detecting an analyte is provided. The nanostructure sensing device comprises at least one nanostructure connected to at least two conductive elements, all disposed over a substrate. There are contact regions adjacent to the connections between the conductive elements and the nanostructure, and inhibiting material covering at least the contact regions. The inhibiting material is impermeable to at least one chemical, biochemical, or biological species. The nanostructure sensing device can further comprise a gate electrode. In one arrangement, there can be a trench in the substrate below at least the at least one nanostructure.

In one arrangement, a portion of the nanostructure is at least partially free of inhibiting material. The inhibiting material may be impermeable to the analyte of interest. The inhibiting material may be impermeable also to such species as moisture, oxygen, ammonia, and nitrous oxide.

In another arrangement, the inhibiting material covers both the contact regions and at least a substantial portion of the nanostructure. The inhibiting material may be semipermeable to the analyte of interest. The thickness of the inhibiting material layer can be chosen to tune selectivity for the analyte of the nanostructure sensing device, that is, to reduce cross-sensitivity. In other arrangements, the thickness of the inhibiting material layer can be chosen to tune sensitivity for the analyte of the nanostructure sensing device.

In one embodiment, a nanotube sensor is provided. The nanotube sensor comprises a plurality of carbon nanotubes disposed over a silicon substrate and at least two metal electrodes in physical and electrical contact with a first nanotube. An inhibiting material covers at least contact regions adjacent to points of the physical contact between the metal electrodes and the first nanotube.

A method of detecting an analyte is also provided. A first electrical signal is measured from a nanostructure sensing device before exposing it to a sensing environment. A second electrical signal is measured from a nanostructure sensing device after exposing it to a sensing environment. Changes between the first electrical signal and the second electrical signal are correlated to detection of the analyte. In one embodiment, the detection can involve detection at ppb or ppm concentrations.

Further features and advantages of the present invention will become apparent to those of ordinary skill in the art in view of the detailed description of preferred embodiments below, when considered together with the attached drawings and claims.

BRIEF DESCRIPTION OF THE DRAWINGS

The foregoing aspects and others will be readily appreciated from the following description of illustrative embodiments when read in conjunction with the accompanying drawings.

DETAILED DESCRIPTION OF THE PREFERRED EMBODIMENT

Figure 1:
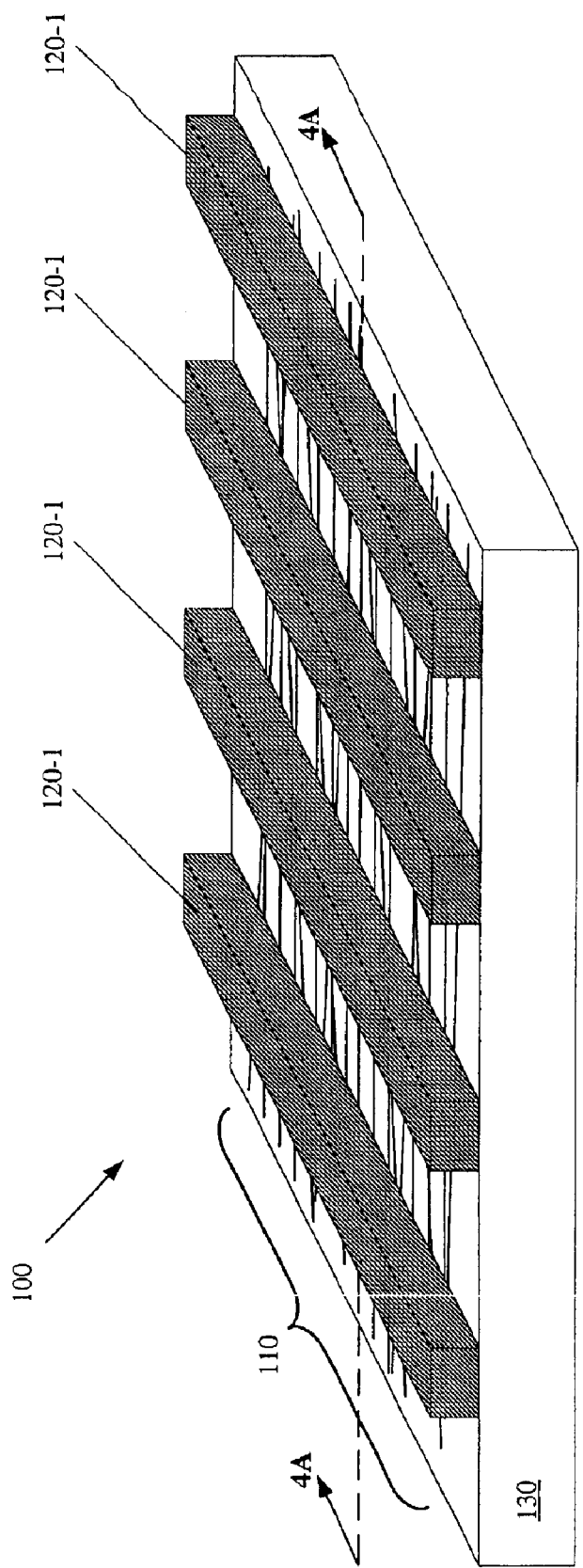
FIG. 1 is a perspective view of a nanotube sensing device.

Carbon nanotubes are usually hollow, elongated structures a few atoms in width with a structure like a sheet of graphite formed into a generally cylindrical configuration. Carbon nanotubes are long molecules, with length to width ratios as large as several thousand or more. They can be formed in furnaces from carbon-containing gases. Carbon nanotubes can form with a single wall, containing just one layer of carbon atoms and having a diameter of one to several nanometers. They can also form with multiple walls, containing a number of hollow cylinders of carbon atoms nested inside one another. They take their name from the nanometer, which is a convenient length for specifying molecular dimensions.

Other elongated nanostructures have also been developed and named by various researchers. These include nanowires, nanofibers, nanorods, and other structures. Nanostructures having an approximately linear form can be arranged in bundles of structures, such as ropes, braids or twisted bundles. Nanostructures can be made of many different elements and compounds. Examples include carbon, boron, boron nitride, and carbon boron nitride, silicon, germanium, gallium nitride, zinc oxide, indium phosphide, molybdenum disulphide, and silver. The composition of a nanostructure can be homogeneous or it can vary throughout the structure. Nanostructures can have cracks, dislocations, branches or other imperfections. Nanostructures can be empty, filled, and multifaceted.

The nanostructures in the embodiments disclosed herein can have approximately linear forms. An approximately linear form can be achieved by using nanostructures that have an approximately linear form naturally, such as nanotubes, nanofibers, nanowires, nanoropes and nanorods. Alternatively, nanostructures having other forms, such as nanospheres, nanocages, nanococoons and nanotori, can be combined with one another or with other nanostructures to create an overall approximately linear form. In general, in this application, when the term "nanotube" is used it should be taken as referring equivalently to such alternative nanostructures as well, which may be adapted similarly for the embodiments described herein.

The embodiments of the invention are illustrated in the context of chemical, biochemical, and biological sensing devices that use nanostructures as the sensing elements. The nanostructures form electrical circuits with conducting electrodes, and sensing events can be detected by changes in the electrical signal through the nanostructure circuit. The materials and methods disclosed herein will have application in a number of other contexts, where control over the sensing system and reproducibility of electrical response is desirable.

These and other objects and advantages of the present invention will become more fully apparent from the following description taken in conjunction with the accompanying drawings.

Nanostructure Sensing Devices

Nanostructures such as nanotubes tend to exhibit quantum rather then classical properties and have the potential to be integrated into semiconductor or silicon platforms to make innovative new electronic devices. One of the properties of single-walled nanotubes made of carbon or other materials is that the electrons flow generally along the surface and are therefore uniquely sensitive to environmental perturbations at the surface. A nanotube has a characteristic electrical resistance that can be measured by applying a voltage. A first electrical signal, such as voltage or current, is measured before a nanotube sensor interacts with an environment. A second electrical signal is measured after a nanotube sensor interacts with the environment. It can be advantageous to apply a gate voltage to the nanotube before measuring the electrical signals. Correlations can be made between known electrical signal changes that occur when known analytes, i.e., targets of analysis or detection, are detected and observed changes between the first signal and the second signal from a nanotube sensing device. The change in electrical properties can be correlated to the analytes that caused the change.

Sensitivity and selectivity of the nanotubes can be enhanced by functionalizing the nanotubes. One way to functionalize a nanotube is to coat it with a recognition layer, a material sensitive to a specific chemical, biochemical, or biological species of interest. Species of interest may include, for example, elements, compounds, molecules, ions, cells, proteins, and bacteria. The recognition layer interacts selectively with the species of interest and can produce an electrical change on the nanotube, which can be measured. The small size of the nanotube can allow recognition of as little as one molecule, and thus can lead to new sensor applications. Recognition layers for a wide variety of chemical sensing can be added to customize sensors for particular sensing needs. A detailed discussion of functionalization of nanostructure sensor devices is given by Gabriel et al. in U.S. patent application Ser. No. 10/099,664, filed Mar. 15, 2002, which is incorporated by reference herein.

The intrinsic advantages of this technology include small size, low power consumption, ultra-sensitivity, and low cost, especially when coupled to conventional semiconductor manufacturing techniques. Nanostructure devices can be made very small; even when a large number of nanostructure devices is arranged in a system array, the size is still very small. Nanostructure sensing devices can be modified to detect a wide variety of chemical species. Until now, nanostructure sensing devices have been made only in small quantities for lab testing. Techniques for producing nanostructure sensing devices have not been developed for large-scale manufacturing.

FIG. 1 is a perspective view of a nanostructure sensing device 100, which illustrates some basic components. A number of nanostructures 110 are arranged over a substrate 130. Note that the bracket collectively refers reference number 110 to each of the individual nanostructures shown in FIG. 1. Conducting elements 120-1, 120-2, 120-3, 120-4 are disposed on the substrate 130 and make electrical contact with the nanostructures 110. There can be any number of conducting elements in contact with the nanostructures 110.

The substrate 130 can be made of any of a variety of materials or layers of materials consistent with the art of semiconductor manufacturing. The substrate 130 can be made of semiconducting materials, such as silicon, III–V compounds, II–VI compounds, or a combination of one or more Group IV elements with any of these. Alternatively, the substrate 430 can be made of an insulating material, such as alumina or quartz.

The nanostructures 110 can be any conducting or semiconducting nanostructures known in the art of nanotechnology. In some embodiments, the nanostructures 110 are nanotubes, nanowires, nanorods, or some other elongated nanostructures. In particular, the nanostructures 110 can be carbon nanotubes and may be single-wall, semiconducting, carbon nanotubes. There can be any number of nanostructures, some of which may intersect one another as they traverse the device 100, and some of which may traverse the device 100 without intersection, as indicated in FIG. 1.

The conducting elements 120-1, 120-2, 120-3, 120-4 can be made of any conductive material. In one embodiment, the conducting elements 120-1, 120-2, 120-3, 120-4 can be lines formed from a lithographic patterning process as is known in the semiconductor arts. In particular, the conducting elements 120-1, 120-2, 120-3, 120-4 can be metal lines formed by such a process. Examples of suitable metals include aluminum, titanium, titanium-tungsten, platinum, gold and copper.

There can be any number n of conducting elements 120-$n$ in contact with the nanostructures 110. FIG. 1 illustrates a nanostructure sensing device 100 that has four conducting elements 120-1, 120-2, 120-3, 120-4. Current can flow in from a conducting element 120-$a$ and out through another conducting element 120-$b$, depending on how the conducting elements 120-$a$, 120-$b$ are connected to outside electrical supplies, as is known in the art of semiconductor device manufacturing. For example, current can flow in from conducting element 120-1, through nanostructures 110, and out through conducting element 120-2. In other examples, current can flow in from conducting element 120-3, through nanostructures 110, and out through conducting element 120-1 or out through conducting elements 120-2 and 120-4. A gate voltage can be applied to the nanostructure sensing device 100.

Some nanostructures 110 can extend beyond an end conducting element 120-1, 120-4. Some nanostructures 110 can end within an end conducting element 120-1, 120-4. Some nanostructures 110 can be much shorter than others and can make contact with fewer than all the conducting elements 120-1, 120-2, 120-3, 120-4.

When an analyte or target species interacts with the nanostructures 110, there can be a change in one or more electrical characteristics of the nanostructures 110. An electrical signal is measured through the nanostructures 110 before exposure to the analyte, and an electrical signal is measured again after the exposure. A change in electrical signal through the nanostructures 110 can be interpreted as an analyte detection event.

The nanostructures 110 themselves can interact easily with some species, such as ammonia. In other cases, the nanostructures 110 can be functionalized for sensing of specific target chemical, biochemical, or biological species. The functionalization can involve coating the nanostructures 110 with recognition layers to achieve a desired interaction with a target species.

Figure 2:
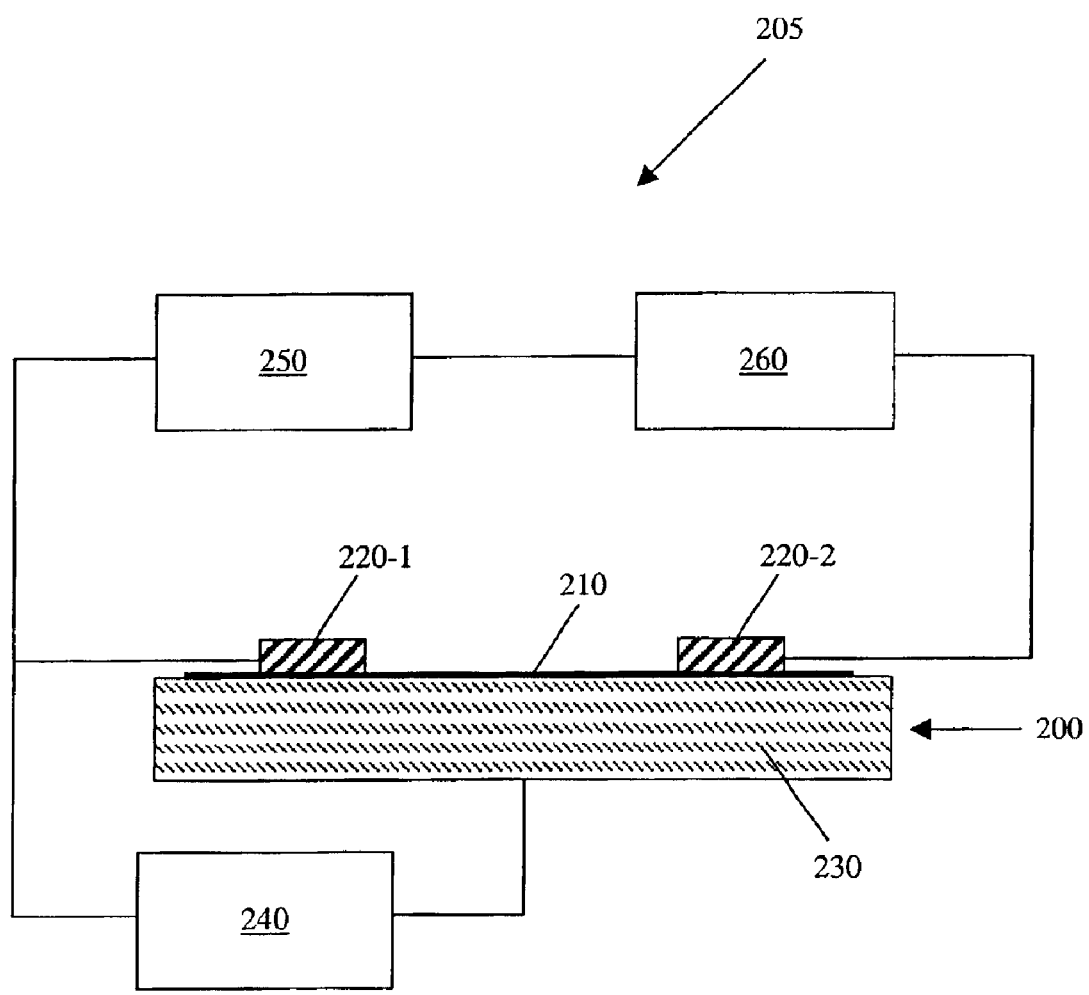
FIG. 2 is a schematic of a nanotube sensing device and other components connected in a circuit.

FIG. 2 is a schematic of a nanostructure sensing device circuit 205 that shows the basic connections and components for measuring electrical signals from a nanostructure sensing device 200. Components of the circuit include an electrical supply 250, a meter 260, and a nanostructure sensing device 200. The electrical supply 250 can be a voltage source, a current source, or a power source and can supply a dc signal, an ac signal, or both. The meter 260 can be an ammeter or a voltmeter. The nanostructure sensing device 200 includes a nanostructure 210 on a substrate 230 and is shown in cross section. Two electrodes 220-1, 220-2 make electrical contact to the nanostructure. A voltage supply 240 can apply a voltage to the substrate 230 that can act as an undifferentiated gate electrode for the device 200. The gate voltage can be dc, ac, or both.

A simple example of how the nanostructure sensing device circuit 205 can be used to detect an analyte is as follows. In a benign environment, the electrical supply 250 applies a first voltage across the nanostructure sensing device 200 and the voltage supply 240 applies a first gate voltage to the substrate 230. A first current through the nanostructure sensing device 200 is measured with the meter 260. The nanostructure sensing device 200 is exposed to an environment of interest. The electrical supply 250 applies the same first voltage across the nanostructure sensing device 200 and the gate voltage source 240 applies the same first gate voltage to the substrate 230. A second current through the nanostructure sensing device 200 is measured with the meter 260. Differences between the first current and the second current can be attributed to electrical changes in the nanostructure sensing device 200 caused by interaction with an analyte. Electrical changes can be correlated to identification of particular analytes by comparing the changes with predetermined electrical changes made in know environments.

Other examples of using the nanostructure sensing device circuit 205 to detect and identify analytes include taking a series of electrical measurements as a function of changing gate voltage or as a function of changing electrical supply 250 voltage or electrical supply 250 current and correlating the results to known measurements from environments containing specific analytes.

Figure 3:
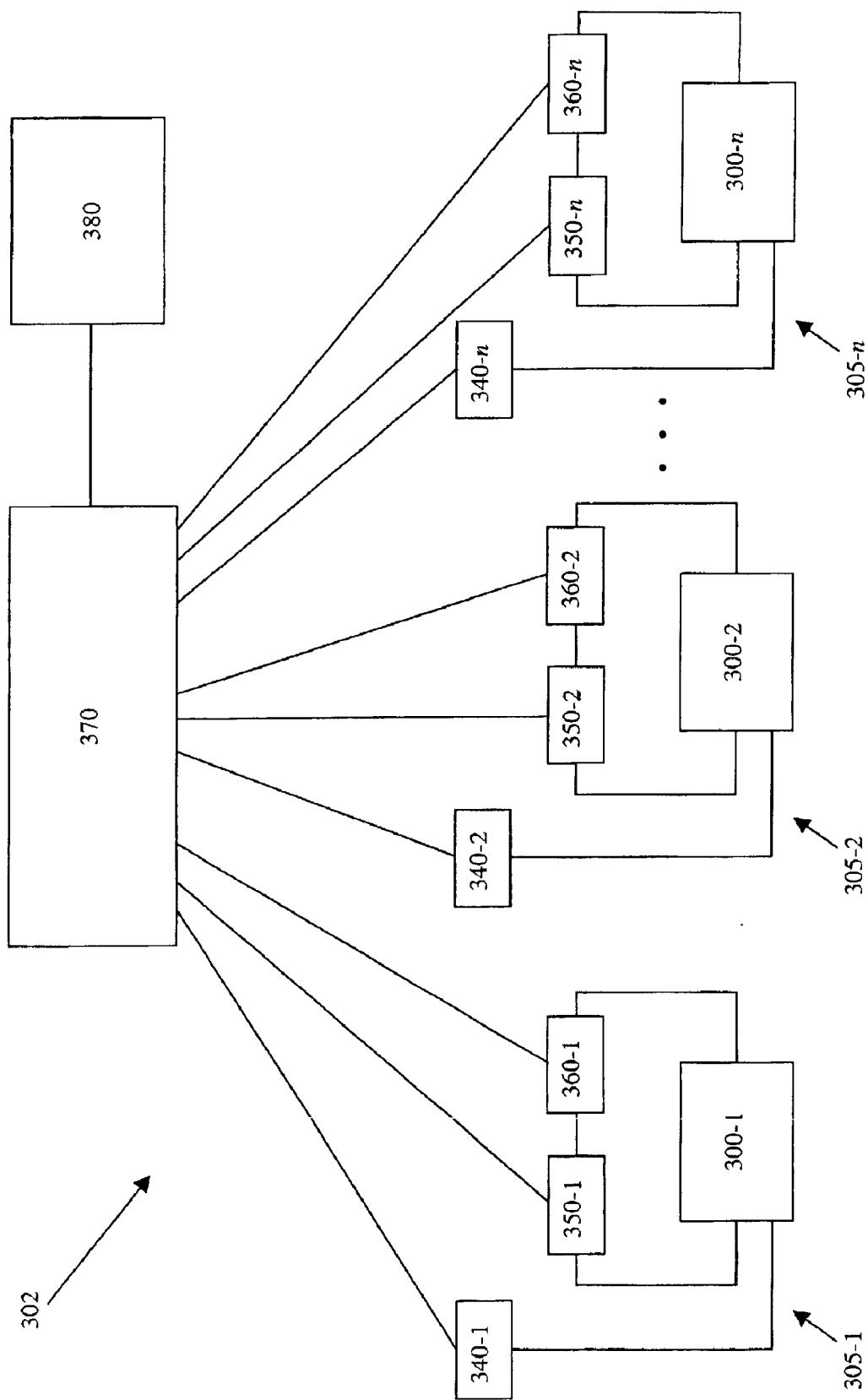
FIG. 3 is a schematic of a system of nanostructure sensing devices connected to a central signal processing unit.

FIG. 3 is a schematic of a system of n nanostructure sensing device circuits 305-1, 305-2, . . . , 305-n connected to a central signal control and processing unit 370. The connections between the device circuits 305-1, 305-2, . . . , 305-n and the central signal control and processing unit 370 may be through electrically conductinve wires of lines, or, in other arrangements, the connections may be wireless. Each nanostructure sensing device circuit 305 includes a nanostructure sensing device 300, a gate voltage source 340, an electrical supply 350, and a meter 360 as has been discussed above for FIG. 2. The central signal control and processing unit 370 can control the gate voltage 340-n and the electrical supply 350-n and can receive meter 360-n measurements for each nanostructure sensing device circuit 305-n. The central signal control and processing unit 370 can include predetermined measurements from nanostructure sensing devices in controlled environments for use in correlating measurements read from nanostructure sensing device circuits 305-n. When it has been determined that a sensing event has occurred, the results can be displayed on the user interface 380.

The n nanostructure sensing device circuits 305-n can include different functionalizations on different devices 300-n or different groups of devices. For example, the nanostructures in nanostructure sensing device circuits 305-1, 305-2, 305-3 (305-3 is not shown) may have functionalization or recognition layers that makes them particularly sensitive to carbon dioxide. The nanostructures in nanostructure sensing device circuits 305-4, 305-5, 305-6 (not shown) may have functionalization or recognition layers that makes them particularly sensitive to hydrogen. The nanostructures in nanostructure sensing device circuits 305-7, 305-8, 305-9 (not shown) may have functionalization or recognition layers that makes them particularly sensitive to nitrous oxide. Measurements from each group of nanostructure sensing device circuits can be sent to the central signal control and processing unit 370 for correlation with known data and determination of whether sensing events have occurred.

Accordingly, the system of FIG. 3 can be configured to sense various analytes. The system itself can be arranged on a semiconductor, silicon, or insulating substrate as an array of nanostructure sensing devices connected to the central signal control and processing unit 370, which is also formed on the substrate using semiconductor manufacturing technology.

Figure 4A:
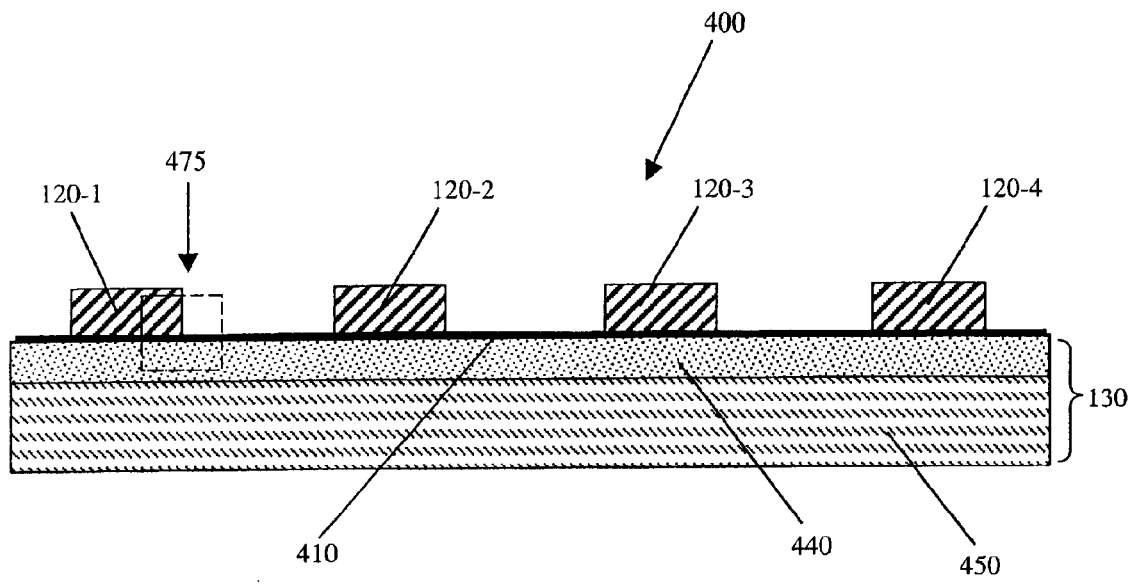
FIG. 4A is a cross section taken along line 4A—4A of the nanotube sensing device shown in FIG. 1.

FIG. 4A is a cross section 400 of the nanostructure sensor 100 in FIG. 1 as cut along line 4A—4A. A nanostructure 410 is in electrical contact with several conducting elements 120-1, 120-2, 120-3, 120-4, all of which are positioned over a substrate 130, which has an top layer 440 over an underlying layer 450. The nanostructure 410 can be any conducting or semiconducting nanostructure known in the art of nanotechnology. In some embodiments, the nanostructure 410 is a nanotube, nanowire, nanorod, or some other elongated nanostructure. In particular, the nanostructure 410 can be a carbon nanotube and may be a single-wall, semiconducting, carbon nanotube. The nanostructure 410 can be in contact with the substrate 130, as shown. Alternatively, the nanostructure 410 can be suspended at least in part above the substrate 130, as will be discussed below.

The substrate 130 can be made of any of a variety of materials or layers of materials consistent with the art of semiconductor manufacturing. The substrate 130 can be made of semiconducting material(s), such as silicon, III–V compounds, II–VI compounds, or a combination of one or more Group IV elements with any of these. Alternatively, the substrate 130 can be made of insulating material(s), such as alumina or quartz. The substrate 130 can contain a top layer 440, which is different from an underlying layer 450. The top layer 440 can be either insulating or semiconducting.

The conducting elements 120-1, 120-2, 120-3, 120-4 can be made of any conductive material. In one embodiment, the conducting elements 120-1, 120-2, 120-3, 120-4 can be lines that are formed from a lithographic patterning process as is known in the semiconductor arts. In particular, the conducting elements 120-1, 120-2, 120-3, 120-4 can be metal lines formed by such a process. There can be any number of conducting elements along the nanostructure 410, as has been discussed above for FIG. 1.

The nanostructure 410 can extend beyond end conducting elements 120-1, 120-4, or the nanostructure 410 can end within either of both end conducting elements 120-1, 120-4. Electrical contact between the nanostructure 410 and the conducting elements 120-1, 120-2, 120-3, 120-4 can be direct, as shown. Alternatively, there can be intervening conducting layers or other components (not shown) between the nanostructure 410 and the conducting elements 120-1, 120-2, 120-3, 120-4.

When an analyte or target species interacts with the nanostructure 410, there can be a change in the electrical characteristics of the nanostructure 410. An electrical signal can be measured through the nanostructure 410 before the interaction, and an electrical signal can be measured again after the interaction. A change in electrical signal through the nanostructure 410 can be interpreted as an analyte detection event. The nanostructure 410 can be functionalized for sensing of specific target chemical, biochemical, or biological species. The functionalization can involve coating the nanostructure 410 with recognition layers to achieve a desired interaction between a target species and the nanostructure 410.

Generally, a material has a Fermi level energy as one of its intrinsic properties. When dissimilar materials, such as a semiconductor and a metal, are brought into contact, a Schottky barrier can be formed. Electric charge flows from one material to the other until the Fermi levels of the dissimilar materials adjust to the same energy. The net result is a charged layer at the barrier. In the absence of additional factors, the electrical properties of the Schottky barrier remain substantially stable once it has formed. One of the factors that can change the electrical character of a Schottky barrier is adsorption of chemical species onto the barrier region. When a chemical species adsorbs onto a material surface, it can modify the electrical charge on the surface, which can change the electrical properties of the contact. The change in electrical properties at the contact can be large enough to produce a signal change that is much larger than a signal change from other portions of the device.

For the purposes of this disclosure, the region near a Schottky barrier along adjacent surfaces over which adsorbed molecules can affect barrier properties will be referred to as the "contact region". The contact region does not have a sharp cut-off point, but extends at least on the order of a few nanometers from the point of contact between the dissimilar materials along adjacent surfaces in all directions. In some embodiments, the contact region extends a distance of at least 1 μm from the point at which the conducting element and the nanostructure make contact. In some arrangements, the contact region extends a distance of at least 50 nm, and in other arrangements a distance of at least 5 nm, from the point at which the conducting element and the nanostructure make physical contact. Other ranges are possible.

Figure 4B:
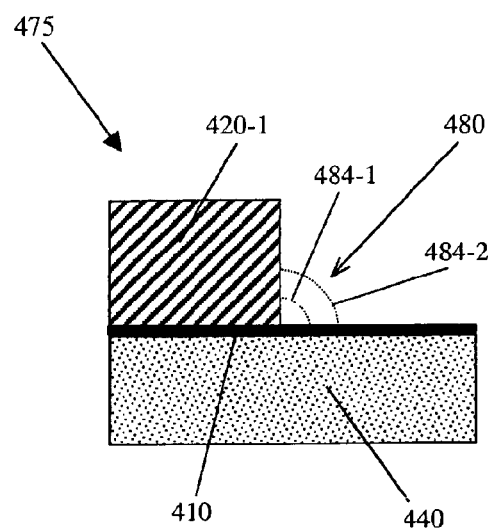
FIG. 4B shows a detailed view of a portion of FIG. 4A.

FIG. 4B is an enlarged view of the dashed area 475 in FIG. 4A. A contact region 480 is associated with a Schottky barrier formed at the physical contact point of the conducting element 420-1 and nanostructure 410. The dotted lines 484-1, 484-2 approximate the extent of the surfaces of the conducting element 420-1 and the nanostructure 410 that comprise the contact region 480. The dotted line 484-1 indicates the extent of the surfaces for which adsorbed molecules would have a strong effect on the electrical properties of the Schottky barrier. The dotted line 484-2 indicates the extent of the surfaces for which adsorbed molecules would have a weaker, but still significant, effect on the electrical properties of the Schottky barrier.

It is useful to understand the sensitivity of the contact region in designing electronic nanostructure devices that contain Schottky barriers. When extreme sensitivity to target species is desired, such as at ppm or ppb levels, sensing at the contact regions adjacent to Schottky barriers can be encouraged. When detection of only higher concentrations is desired, e.g., 5% or more, the contact regions adjacent to Schottky barriers can be covered with an inhibiting or passivation material to prevent species from adsorbing onto the contact regions. In other cases the entire nanostructure sensing device can be covered with a semi-permeable, inhibiting layer to shield the device at least partially from some species while allowing other species to pass through. The thickness of a semi-permeable layer can be adjusted to allow only a portion of a desired species to reach the nanostructure sensing device and thus to tune the sensitivity of detection.

Maximizing Contact Region Area

The Schottky barrier that forms when a metal and a semiconductor are joined can be extremely sensitive to adsorbed gases. As discussed above, a chemical species adsorbed onto a material surface can modify the electrical charge on the surface. When charge is modified in the contact region adjacent to a Schottky barrier, the electrical properties of the barrier can be changed. In the embodiments described below, the sensitivity of the contact region around the Schottky barrier is used to advantage in nanostructure sensing devices to detect analytes or target species at concentrations as low as parts per million (ppm) or parts per billion (ppb).

Figure 5A:
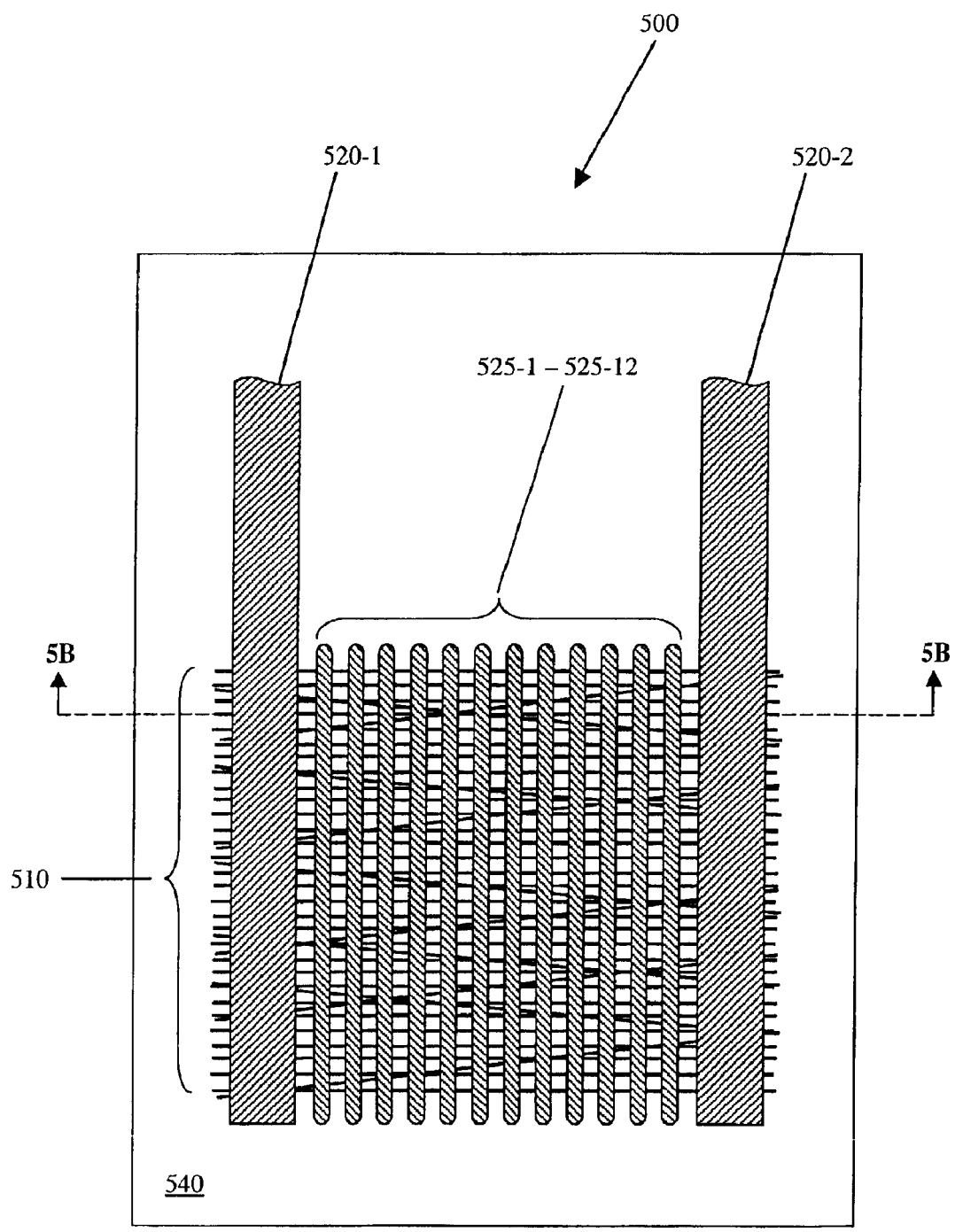
FIG. 5A is a top view of a nanostructure sensing device configured to increase Schottky barrier contact region area.
Figure 5B:
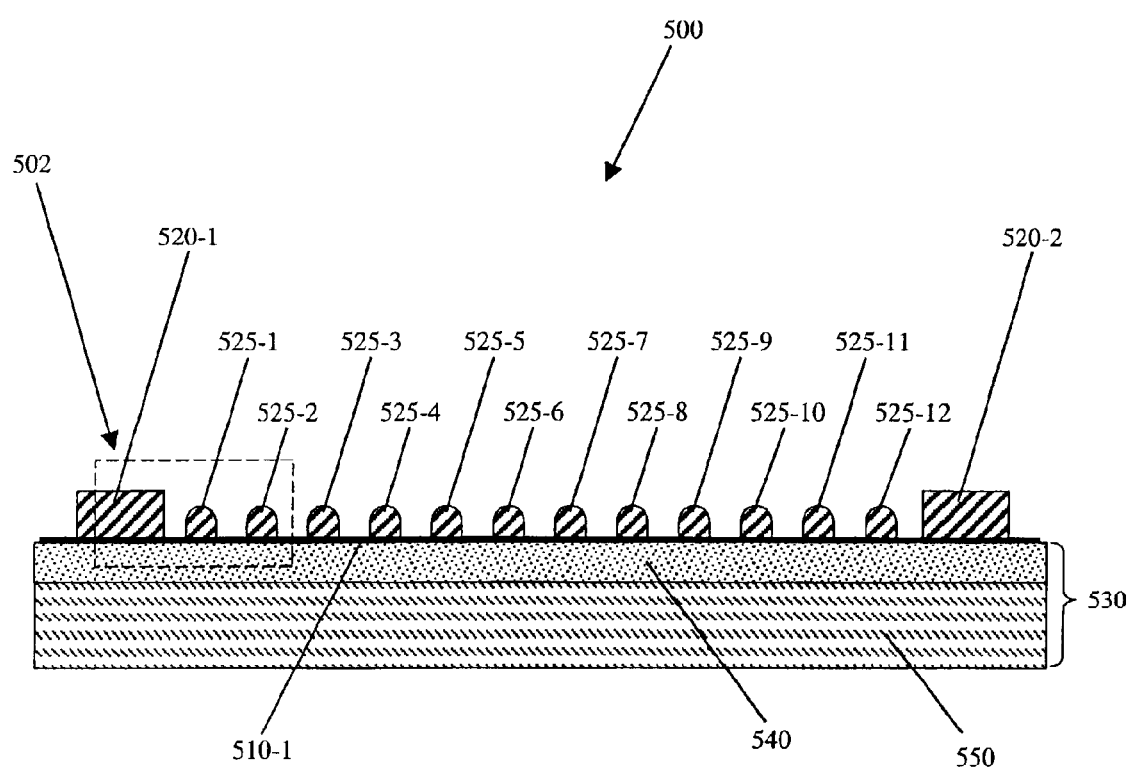
FIG. 5B is a cross section taken along line 5B—5B of the nanostructure sensing device shown in FIG. 5A.
Figure 5C:
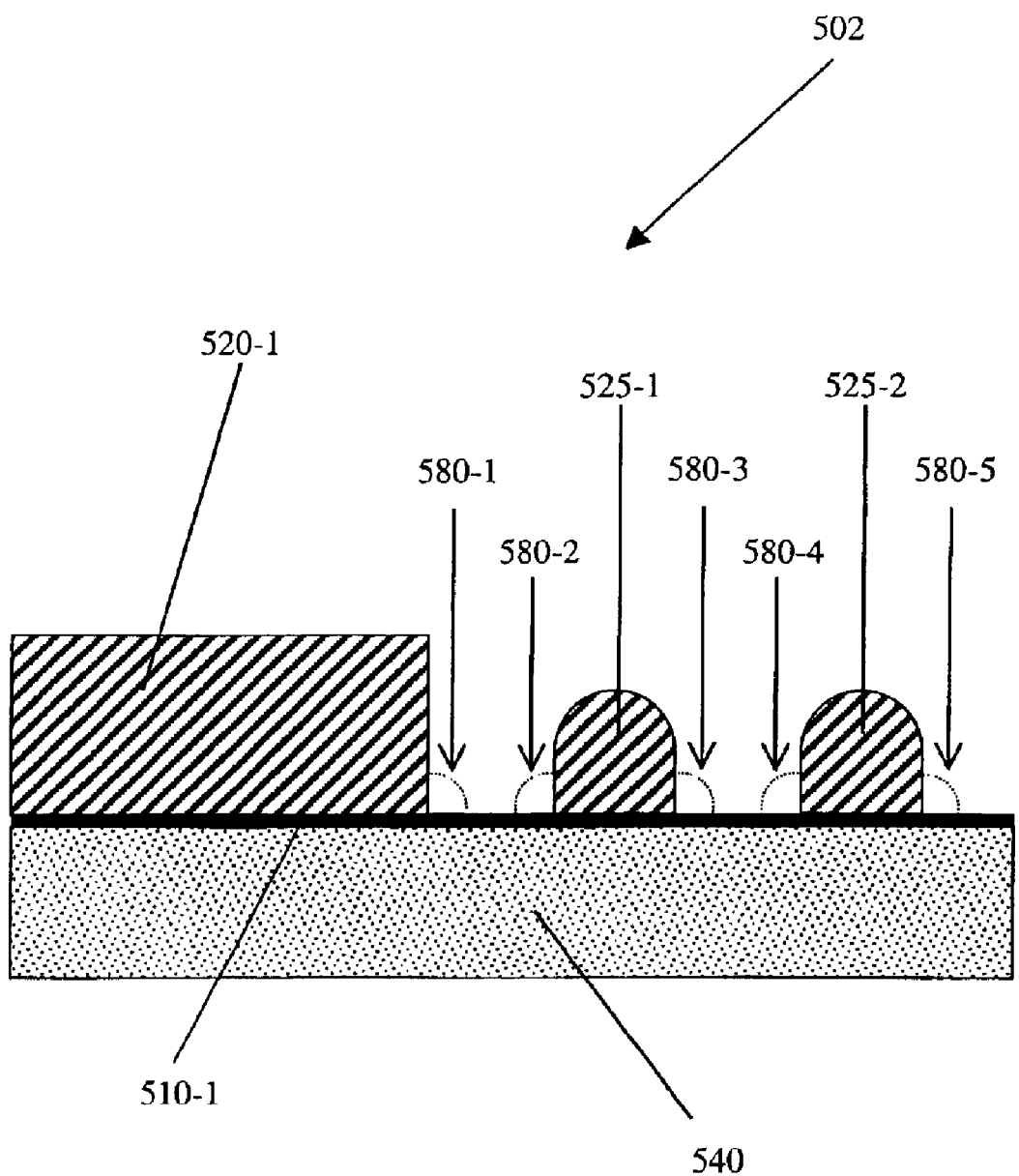
FIG. 5C is a detail of the cross section of FIG. 5B.

FIGS. 5A, 5B, 5C illustrate a nanostructure sensing device 500 in an arrangement that has a larger ratio of contact region surface area to exposed nanostructure surface area than for arrangements such as the one illustrated in FIG. 1.

The nanostructure sensing device 500 in FIG. 5A has, as its base, a nanostructure sensing device as has been described above in FIGS. 1 and 4A. FIG. 5A is a top view that shows one or more nanostructures 510 arranged on a top layer 540 of a substrate. Note that the bracket collectively refers reference number 510 to each of the individual nanostructures shown in FIG. 5A. There are two conducting elements 520-1, 520-2 in contact with the nanostructures 510. In other arrangements, there can be n additional conducting elements 520-3–520-n. (not shown). The conducting elements 520-1, 520-2 can be connected to a electrical supply (not shown) to allow formation of an electrical circuit that includes the nanostructures 510. In this example, there are twelve nodes 525-1–525-12 which are made of a material different from the nanostructure 510 material and are in contact with the nanostructures 510. In other arrangements, there may be only one or there may be any number n of nodes 525-1–525-n. The nodes 525-1–525-12 can be made of the same material as the conducting elements 520-1, 520-1, or they can be made of different materials. In some arrangements, the nodes 525-1–525-12 are metal. FIG. 5A shows the conducting elements 520-1, 520-2 and the nodes 525-1–525-12 with different shapes. The shapes have been used only for the purpose of illustration to indicate that the conducting elements 520-1, 520-2 and the nodes 525-1–525-12 can have different electrical functions, i.e., the conducting elements 520-1, 520-1 can be connected to an electrical supply. Both the conducting elements 520-1, 520-2 and the nodes 525-1–525-12 can have any configuration that allows them to make contact to at least some of the nanostructures 510.

FIG. 5B is a cross-sectional view of the nanostructure sensing device 500 as cut through a nanostructure 510-1 along the line 5B—5B indicated in FIG. 5A. Schottky barriers can form at junctions of dissimilar materials, such as at the junctions of conducting elements 520-1, 520-2 and the nanostructure 510-1 and at junctions of nodes 525-1–525-12 and the nanostructure 510-1. As the density of Schottky barriers along the nanostructure 510-1 increases, the proportion of nanostructure surface area that is within contact regions also increases.

FIG. 5C is an enlarged view of the dashed area 502 in FIG. 5B. Schottky barriers can form both at junctions of the conducting element 520-1 and the nanostructure 510-1 and at junctions of the nodes 525-1, 525-2 and the nanostructure 510-1. The regions near the Schottky barriers along adjacent surfaces and over which adsorbed molecules can affect barrier properties are indicated by contact regions 580-1, 580-2, 580-3, 580-4, 580-5. The contact regions do not have sharp end points, but extend from the junctions along adjacent surfaces in all directions, as has been described above in FIG. 4B.

In some embodiments, the contact region extends a distance of at least 1 μm from the point at which the dissimilar materials make physical contact. In some arrangements, the contact region extends a distance of at least 50 nm, and in other arrangements a distance of at least 5 nm, from the point at which the dissimilar materials make physical contact. Other ranges are possible. The dotted line corresponding to each contact region 580-1–580-5 indicates approximately the extent of each contact region 580-1–580-5 along the surface of the conducting element 520-1, along the surfaces of the nodes 525-1, 525-2, and along the surface of the nanostructure 510-1.

With reference to FIGS. 5B and 5C, as the number n of nodes 525-1–525-n increases, the number m of contact regions 580-1–580-m increases also. As the number m of contact regions 580-1–580-m increases, the total surface area of the contact regions 580-1–580-m increases and the total surface area of the adjacent non-contact region nanostructure 510-1 decreases. Thus, the component of the electrical signal that comes from the contact regions 580-1–580-m increases, and the component of the electrical signal that comes from the non-contact region area of nanostructure 510-1 decreases. Electrical signals measured from the nanostructure 510-1 include contributions from both the contact regions 580-1–580-m and the adjacent non-contact region surfaces of the nanostructure 510-1. As the density of nodes 525-1–525-n increases, the electrical signal can become dominated by contributions from the contact regions 580-1–580-m. Electrical signal changes can be due mainly to sensing events that occur in the contact regions.

Figure 6:
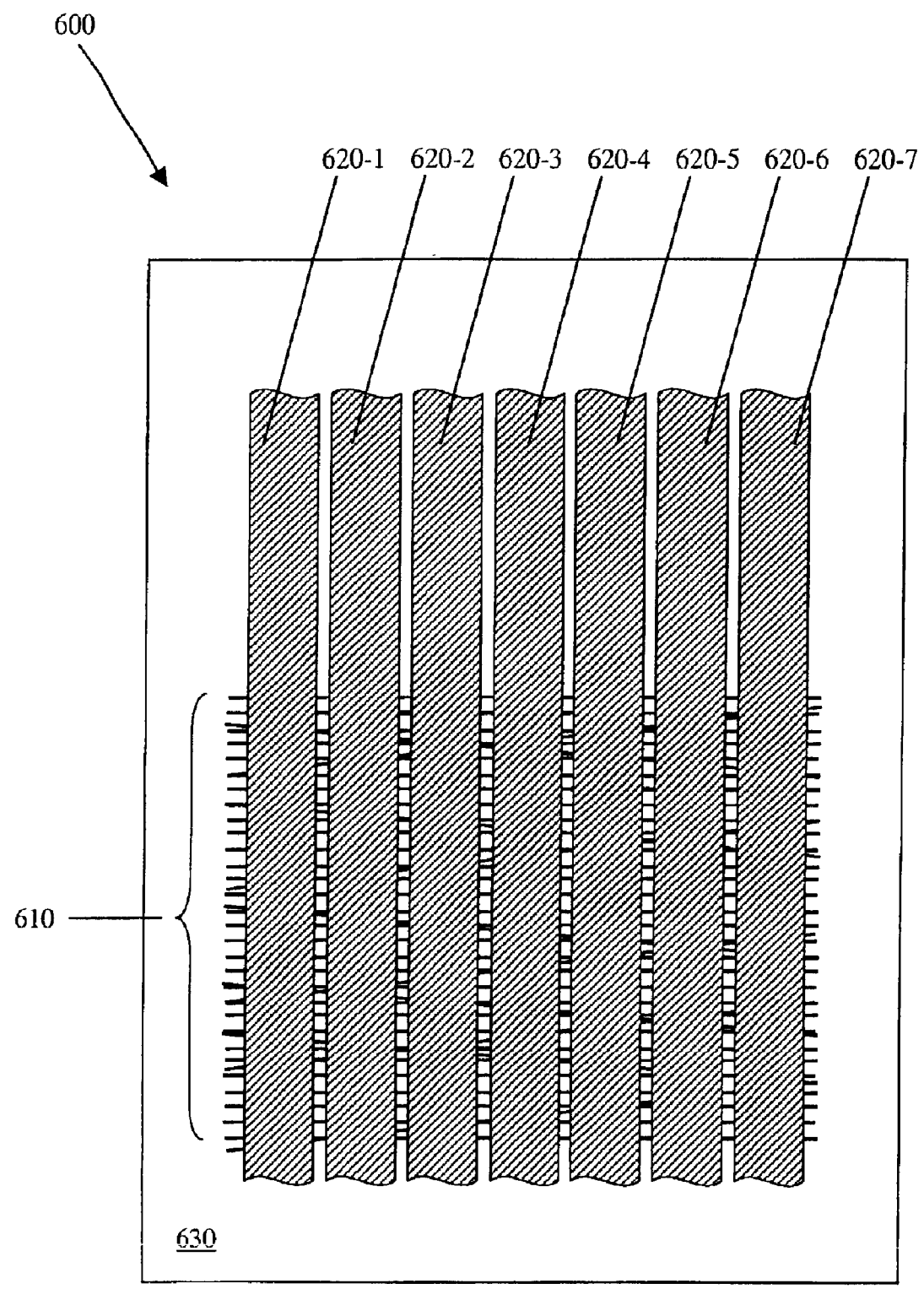
FIG. 6 is a top view of a nanostructure sensing device in another configuration designed to increase Schottky barrier contact region area.

Another arrangement for increasing contact region relative to non-contact region nanostructure surface area is illustrated in the arrangement of nanostructure sensing device 600 shown in top view in FIG. 6.

A plurality of nanostructures 610 are arranged over a substrate 630. Note that the bracket collectively refers reference number 610 to each of the individual nanostructures shown in FIG. 6. Several closely-spaced, conducting lines 620-1–620-7 make contact to the nanostructures 610. In some arrangements, the conducting lines 620-1–620-7 are metal. There can be any number n of conducting lines 620-1–620-n. Conducting lines 620-1–620-n can be connected to electrical supplies (not shown) in various ways, as is known in the semiconductor device arts. Schottky barriers can form at junctions between the metal lines 620-1–620-7 and semiconducting nanostructures 610. As has been discussed above, contact regions extend from the junctions of dissimilar materials, such as the conducting lines 620-1–620-7 and the semiconducting nanostructures 610.

In some embodiments, the contact regions extend a distance of at least 1 μm from the point at which the dissimilar materials, i.e., the conducting elements 620-1–620-7 and the nanostructures 610 make physical contact. In some arrangements, the contact region extends a distance of at least 50 nm, and in other arrangements a distance of at least 5 nm, from the point at which the dissimilar materials, i.e., the conducting elements 620-1–620-7 and the nanostructures 610 make physical contact. Other ranges are possible. The dotted line corresponding to each contact region 580-1–580-5 indicates approximately the extent of each contact region 580-1–580-5 along the surface of the conducting element 520-1, along the surfaces of the nodes 525-1, 525-2, and along the surface of the nanostructure 510-1.

As the density of conducting elements 620-1–620-7 increases, the density of Schottky barriers increases, and the proportion of surface area within the contact regions relative to non-contact region surface area along the nanostructures 610 also increases. Electrical signals measured from sensing device 600 include contributions from both the contact region portions of the nanostructures 610 and the portions of the nanostructures 610 adjacent to the contact regions. As the contact region portions increase and the adjacent nanostructure portions decrease, the electrical signal can become dominated by contributions from the contact regions. Electrical signal changes can be due mainly to sensing events that occur in the very sensitive contact regions.

Nanostructure sensing devices such as those shown in FIGS. 5 and 6, or in any other configuration where a large proportion of the nanostructure surface area is within contact regions can be especially useful for detection of analytes at very low concentrations, such as at ppm or ppb levels.

Passivated Contacts

Figure 7A:
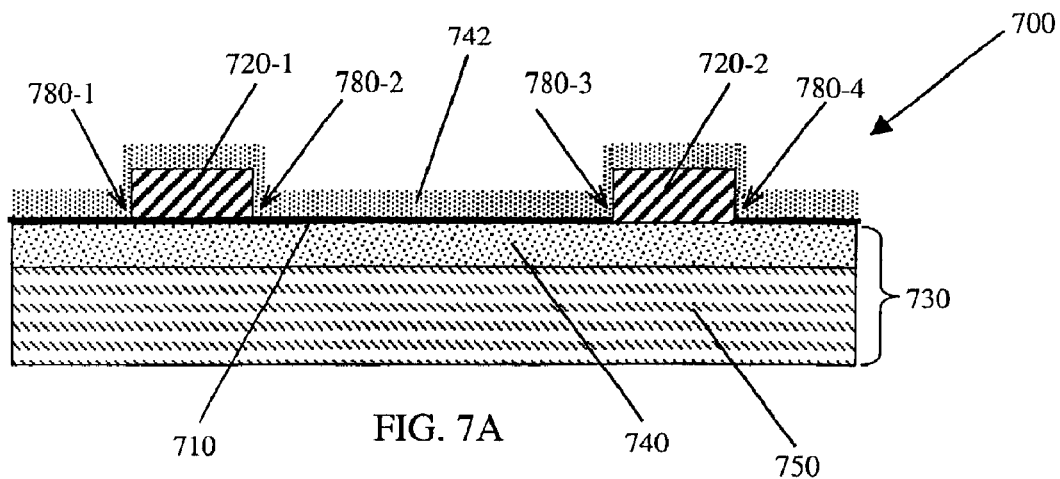
FIG. 7A is a cross section of a nanotube sensing device that has a first layer of passivation material covering at least a portion of the device.

FIG. 7A shows, in cross section, a nanostructure sensing device 700 that has a nanostructure 710 in electrical contact with two conducting elements 720-1, 720-2, all over a substrate 730. The nanostructure 710 can be any conducting or semiconducting nanostructure known in the art of nanotechnology, as discussed above in reference to FIG. 1. The conducting elements 720-1, 720-2 can be made of any conductive material, as has been discussed above in reference to FIG. 1. There can be just two conducting elements 720-1, 720-2, as shown, or there can be any number n of conducting elements 720-1–720-n along the length of the nanostructure 710. The substrate 730 can be made of any of a variety of materials consistent with the art of semiconductor manufacturing, as has been discussed above in reference to FIG. 1. The substrate 730 can contain an insulating or semiconducting layer as a top layer 740, which is different from an underlying layer 750. Electrical contact between the nanostructure 710 and the conducting elements 720-1, 720-2 can be direct as shown. Alternatively, there can be intervening conducting layers or other components (not shown) between the nanostructure 710 and the conducting elements 720-1, 720-2.

There is a first layer of passivation or inhibiting material 742 over the nanostructure 710 and conducting elements 720-1, 720-2. The first passivation or inhibiting layer 742 can be any material that is electrically insulating. In some arrangements, the passivation layer 742 is substantially impermeable to water. In some arrangements, the passivation layer 742 is substantially impermeable to at least some chemical and biological species. The passivation layer 742 can be deposited using a thermal, resistive, electron-beam evaporation technique, or low temperature chemical vapor deposition, or by other methods. In some embodiments, the passivation layer 742 may be, for example, silicon oxide deposited by electron-beam evaporation. In general, evaporation techniques are slow and are highly directional and produce layers that do not have good conformality, as indicated in the example passivation layer 742 in FIG. 7A, wherein vertical portions are thinner than horizontal portions. On the other hand, evaporation techniques are relatively benign and tend not to harm nanostructures such as carbon nanotubes. The thickness of the first passivation layer 740 may be between about 5 nm and 100 nm. In some arrangements, the thickness of the first passivation layer 740 can be between about 10 nm and 30 nm.

The first inhibiting layer 742 shown on device 700 in FIG. 7A can be at least partially permeable to a species of interest. Embodiments that employ a semipermeable layer will be discussed in detail with respect to FIGS. 10A and 10B. Alternatively, the first inhibiting layer 742 can be a first processing step for producing structures 702 and 704, shown in FIGS. 7B and 7C, respectively.

Figure 7B:
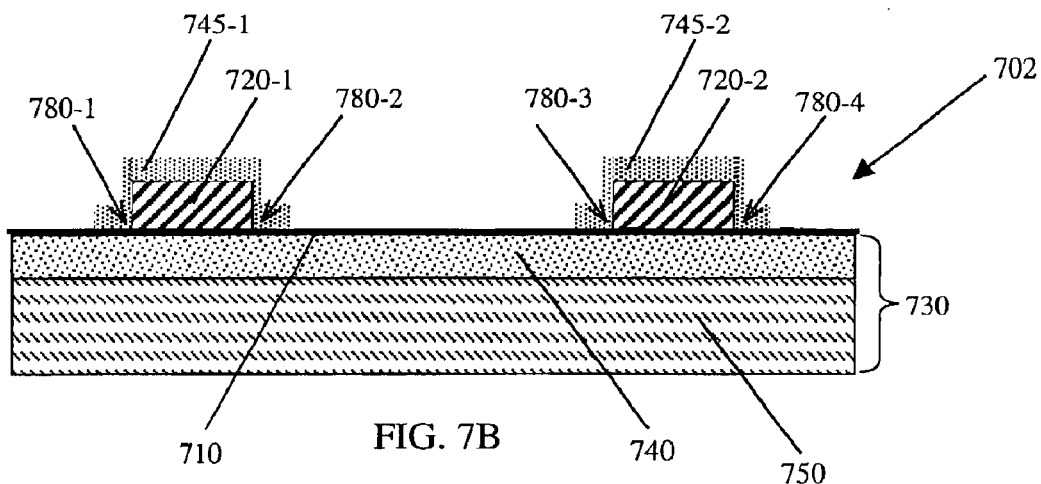
FIG. 7B is a cross section of a nanotube sensing device that has a first layer of passivation material substantially covering the depicted conducting elements and contact regions.

FIG. 7B shows a nanostructure sensing device 702 much like the nanostructure sensing device 700 of FIG. 7A with some portions of the first passivation layer 742 removed to expose sections of the nanostructure 710. Portions of the first passivation layer 742 can be removed by a pattern and etch process. The first layer 742 portions can be removed by any etch process that does not harm the nanostructure 710. Buffered oxide etch (BOE), which is well-known in the semiconductor arts, can be used as a wet etch agent for silicon oxides. Remaining portions 745-1, 745-2 of the first passivation layer cover at least a substantial portion of contact regions 780-1, 780-2, 780-3, 780-4. The passivation portions 745-1, 745-2 can extend along the surfaces of the conducting elements 720-1, 720-2 and along the surfaces of the nanostructure 710 a distance of at least 1 $\mu$m from the points at which the conducting elements 720-1, 720-2 and nanostructure 710 make physical contact. In other arrangements, the passivation portions 745-1, 745-2 can extend along the surfaces of the conducting elements 720-1, 720-2 and along the surfaces of the nanostructure 710 a distance of at least 50 nm, or a distance of at least 5 nm, from the points at which the conducting elements 720-1, 720-2 and nanostructure 710 make physical contact.

The nanostructure sensing device 702 shown in FIG. 7B has a relatively thin layer of passivation 745-1, 745-2 mainly on the contact regions 780-1–780-4. A large portion of the nanostructure 710 is substantially free of passivation material. The contacts are passivated with only a minimum of processing, thus saving time and money in processing. This embodiment can be useful, for example, for sensing in environments that are not particularly reactive with nanostructure sensing devices. Chemical, biochemical, or biological species that are very aggressive may be able to breech the thin layer of passivation material provide in nanostructure sensing device 702.

Figure 7C:
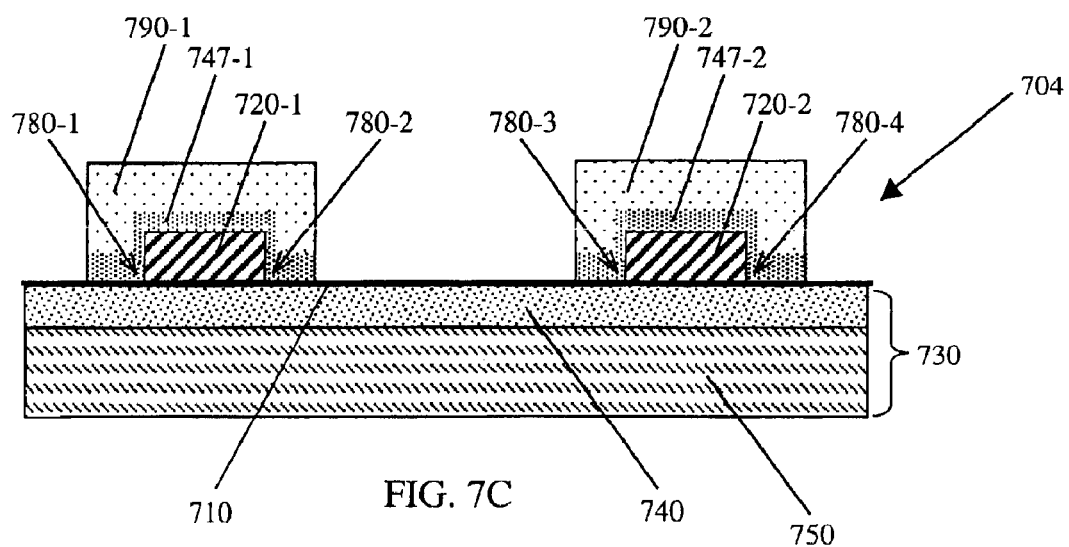
FIG. 7C is a cross section of a nanostructure sensing device that has a first layer of passivation and a second layer of passivation substantially covering the depicted conducting elements and contact regions.

The nanostructure sensing device 704 in FIG. 7C shows another passivation scheme for a nanostructure sensing device. The passivated nanostructure sensing device 704 has, as its base, a nanostructure sensing device 100 as has been described above in FIG. 1. Contact region 720-1 is covered by portions 747-1, 790-1 of passivation material. Similarly, contact region 720-2 is covered by portions 747-2, 790-2 of passivation material.

A first passivation or inhibiting layer 747 is deposited over the nanostructure sensing device. The first passivation layer 747 can be any material that is electrically insulating. In some arrangements, the passivation layer 747 is substantially impermeable to water. In some arrangements, the passivation layer 747 is substantially impermeable to at least some chemical and biological species. The passivation layer 747 can be deposited using a thermal, resistive, or electron-beam evaporation technique or by low temperature chemical vapor deposition. In some arrangements, the passivation layer 747 is silicon oxide deposited by electron-beam evaporation. In general, evaporation techniques are slow, are highly directional and produce layers that do not have good conformality, as indicated in the example passivation layer 747 in FIG. 7C, wherein vertical portions are thinner than horizontal portions. On the other hand, evaporation techniques are relatively benign and tend not to harm nanostructures such as carbon nanotubes. In one arrangement, the thickness of the first passivation layer 747 is between about 5 nm and 100 nm. In another arrangement, the thickness of the first passivation layer 747 is between about 10 nm and 30 nm.

A second layer 790 of passivation or inhibiting material is deposited over the first layer 747. The second passivation layer 790 can be any material that is electrically insulating. In some arrangements, the second passivation layer 790 is substantially impermeable to water. In some arrangements, the second passivation layer 790 is substantially impermeable to at least some chemical and biological species. The second passivation layer 790 can be silicon oxide. In some arrangements, the second passivation layer 790 is deposited using processes such as plasma-enhanced chemical vapor deposition (PECVD) and sputtering, which are fast, are not highly directional and produce layers that have good conformality, as indicated in the example passivation layer 790 in FIG. 7C.

Portions of the passivation layers 747, 790 over the nanostructure 710 can be removed by any etch process that does not harm the nanostructure 710. Buffered oxide etch (BOE), which is well-known in the semiconductor arts, can be used as a wet etch agent for silicon oxides. Remaining portions 747-1, 747-2, 790-1, 790-2 of the first and second passivation layer cover at least a substantial portion of contact regions 780-1, 780-2, 780-3, 780-4. The passivation portions 747-1, 747-2, 790-1, 790-2 can extend along the surfaces of the conducting elements 720-1, 720-2 and along the surfaces of the nanostructure 710 a distance of at least 1 $\mu$m from the points at which the conducting elements 720-1, 720-2 and nanostructure 710 make physical contact. In other arrangements, the passivation portions 747-1, 747-2, 790-1, 790-2 can extend along the surfaces of the conducting elements 720-1, 720-2 and along the surfaces of the nanostructure 710 a distance of at least 50 nm, or a distance of at least 5 nm, from the points at which the conducting elements 720-1, 720-2 and nanostructure 710 make physical contact. Substantial portions of the nanostructure 710 are free of first 747 and second 790 passivation layers and thus can be exposed to an outside environment.

The sides of the conducting elements 720-1, 720-2 that are not in contact with the substrate 730 can be covered by the portions of the passivation or inhibiting materials 747-1, 747-2, 790-1, 790-2, as shown in FIG. 7C. The passivation portions 747-1, 747-2, 790-1, 790-2 can extend along the nanostructure 710 and into and out of the page along the conducting elements 720-1, 720-2 to cover at least a substantial portion of the contact regions 780-1, 780-2, 780-3, 780-4.

In general, plasma and sputtering deposition methods are desirable because they can deposit high quality layers quickly, but they can damage nanostructures. The first passivation layer 747 can provide protection for the nanostructure 710 during PECVD or sputtered depositions. The second passivation layer 790 covers the first passivation layer 747, and a relatively thick layer can be deposited quickly. In one embodiment, the thickness of the second passivation layer 790 is between about 100 nm and 500 nm. In another embodiment, the thickness of the second passivation layer 790 is between about 125 nm and 200 nm.

The nanostructure sensing device 704 shown in FIG. 7C has a relatively thick passivation that includes portions 747-1, 747-2 of the first passivation layer and portions 790-1, 790-2 of the second passivation layer. The passivation is mainly on the contact regions 780-1–780-4. A large portion of the nanostructure 710 is substantially free of passivation material. The contact regions are covered with a thick passivation layer using a method that involves two main processing steps. A thin layer 747 is deposited first to protect the nanostructure from subsequent processing. The thin layer 747 can be deposited using an evaporation technique. Evaporation techniques deposit films slowly, and are not most efficient when thick layers are desired. A second thick layer 790 can be deposited more quickly by using techniques such as PECVD or sputtering. This embodiment can be useful, for example, for sensing in hostile environments. The thick layer of passivation may protect the contact regions from chemical, biochemical, or biological species that are very aggressive.

Figure 8:
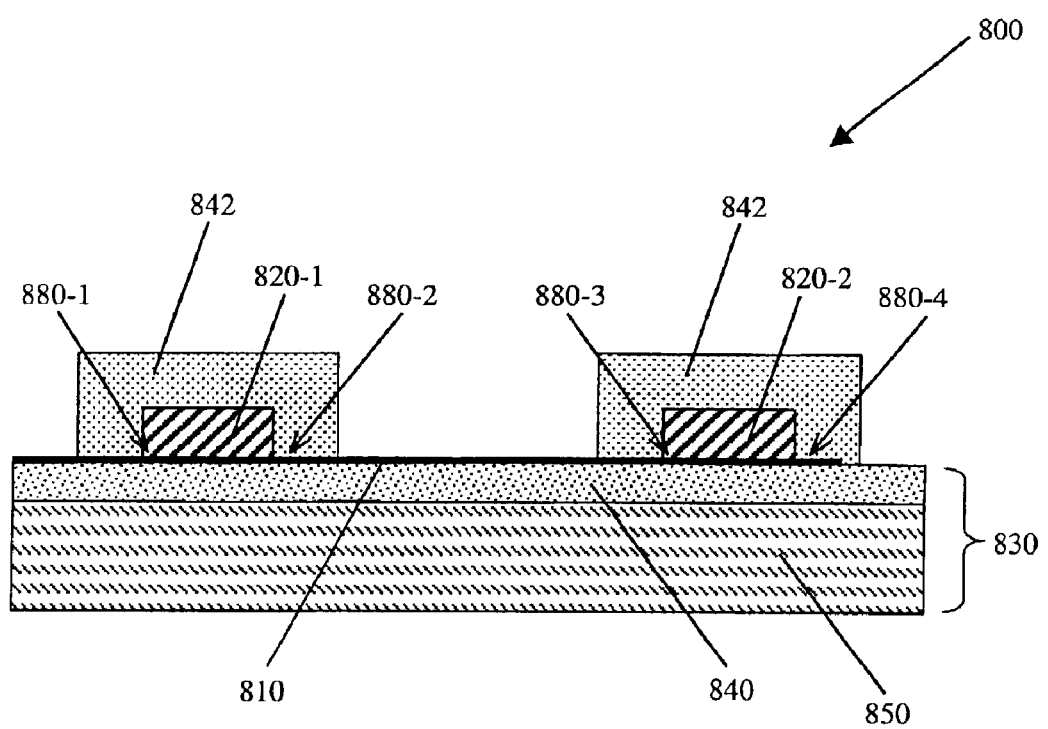
FIG. 8 is a cross section of a nanostructure sensing device with a single layer of passivation material that has been patterned and etched to expose a substantial portion of the nanostructure.

FIG. 8 shows a passivated nanostructure sensing device 800, in cross section, which has been passivated according to an embodiment of the invention. The passivated nanostructure sensing device 800 has, as its base, a nanostructure sensing device as has been described above in FIG. 1. Conducting elements 820-1, 820-2 are positioned adjacent top layer 840 of substrate 830. Passivation or inhibiting material portions 842-1, 842-2 cover at least the contact regions 880-1, 880-2, 880-3, 880-4 and can extend along the nanostructure 810 and into and out of the page along the conducting elements 820-1, 820-2. The passivation material 842 can be deposited by any of a number of processes, such as plasma-enhanced chemical vapor deposition (PECVD), sputtering, evaporation by thermal, resistive, and electron-beam means, and chemical vapor deposition. In one embodiment, the thickness of the passivation layer 842 is between about 75 nm and 500 nm. In another embodiment, the thickness of the passivation layer 842 is between about 100 nm and 200 nm.

The nanostructure sensing device 800 shown in FIG. 8 has a relatively thick passivation that includes portions 842-1, 842-2 of the passivation material. The passivation covers at least the contact regions 880-1–880-4. A large portion of the nanostructure 810 is substantially free of passivation material. The contact regions are covered with one thick passivation layer. It can be more efficient and cost effective to deposit the passivation using only one layer. For nanostructures 810 that are not harmed by deposition techniques that deposit thick layers quickly, or for devices where thick layers are desired in spite of the time required for deposition, this embodiment can be useful This embodiment can be useful, for example, for sensing in hostile environments. The thick layer of passivation may protect the contact regions from chemical, biochemical, or biological species that are very aggressive.

When the nanostructure and the substrate are in contact with one another, undesirable chemical interactions can occur. For example, if the top layer of the substrate is a dielectric material, elements within the dielectric can migrate to the nanostructure and cause it to become doped, thus changing the electrical behavior of the nanostructure. In another example, if the substrate has its own sensitivity to chemical, biochemical or biological species in the surrounding environment, interactions between the substrate and the species can affect the electrical behavior of the nanostructure sensing device in a way that is difficult to control or to factor out.

Figure 9:
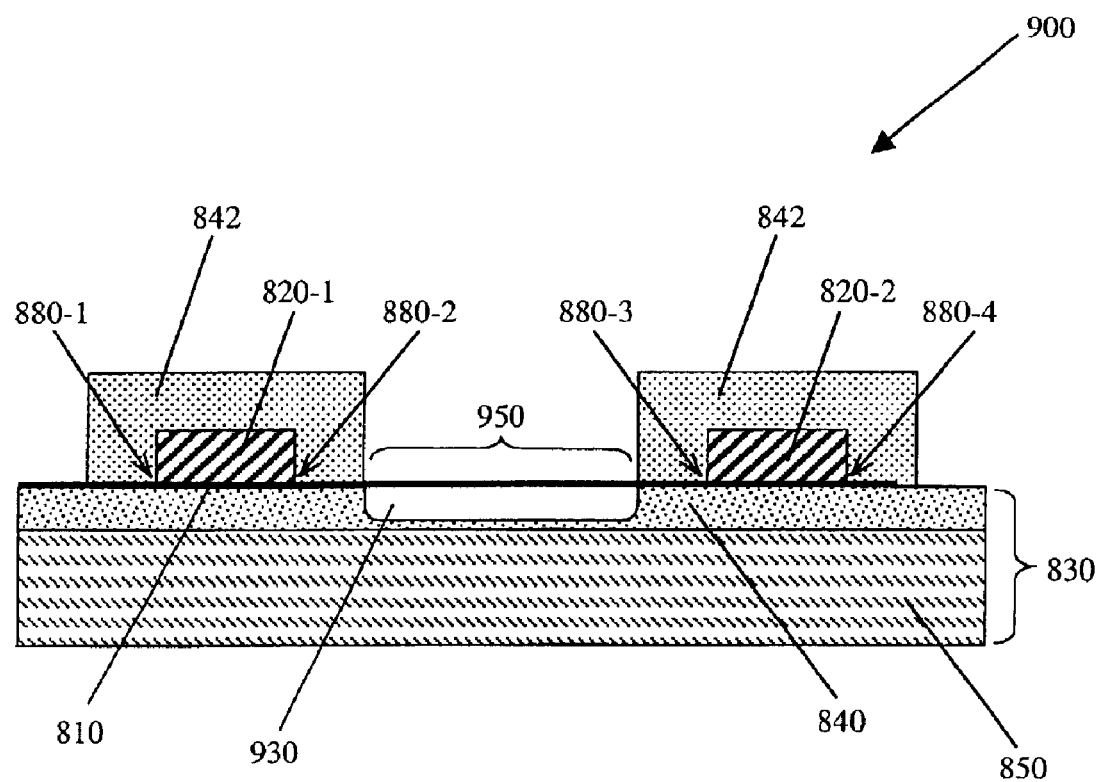
FIG. 9 shows the nanostructure sensing device of FIG. 6 with a trench below a substantial portion of the nanostructure.

FIG. 9 shows a nanostructure sensing device 900 with a structure that can mitigate substrate effects. FIG. 9 shows the nanostructure sensing device 800 of FIG. 8 with a trench 930 in the top layer 840 of the substrate 830 below a section 950 of the nanostructure 810 in an embodiment of the invention. The trench 930 isolates the section 950 of the nanostructure 810 to reduce contact between the top layer 840 of the substrate 830 and the nanostructure section 950. The trench 930 can be formed by wet etching, by dry etching, or by any method that will remove substrate material 840, 830 without harming the nanostructure 810. Buffered oxide etch (BOE), which is well known in the semiconductor arts, can be used as a wet etch agent for silicon oxides. Dry etch gases such as xenon difluoride ($XeF_2$) can be used to etch silicon. In one embodiment, the depth of the trench is between about 1 nm and 1 µm. In another embodiment, the depth of the trench is between about 10 nm and 100 nm.

Semi-Permeable Passivation

Figure 10A:
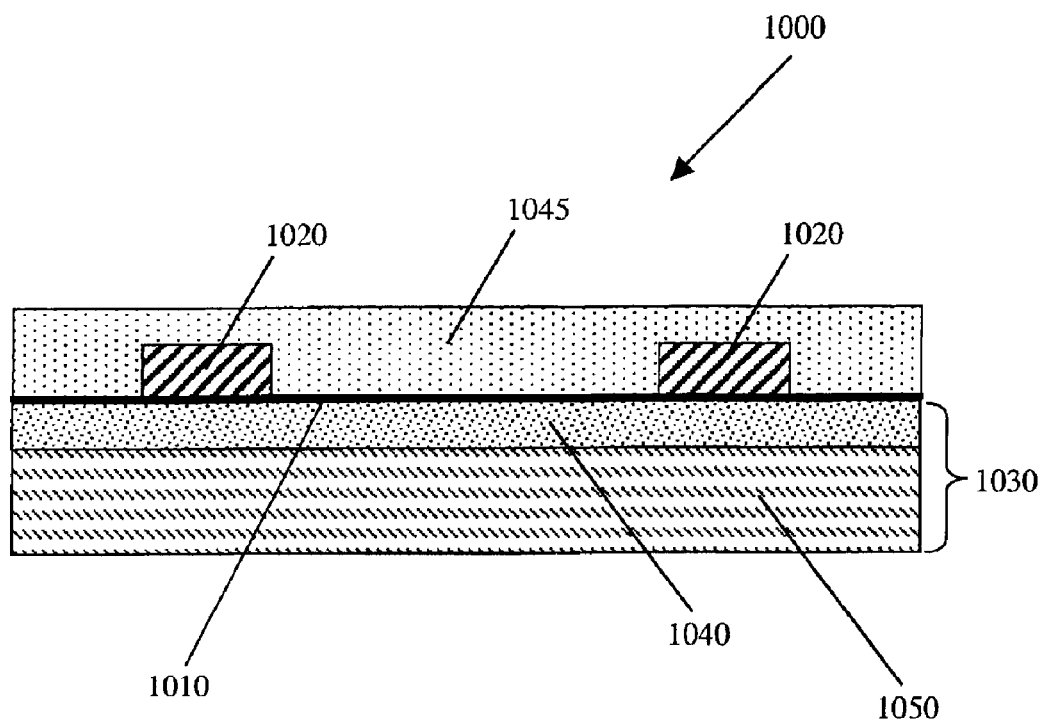
FIG. 10A is a cross section of a nanostructure sensing device with a layer of semipermeable inhibiting material.
Figure 10B:
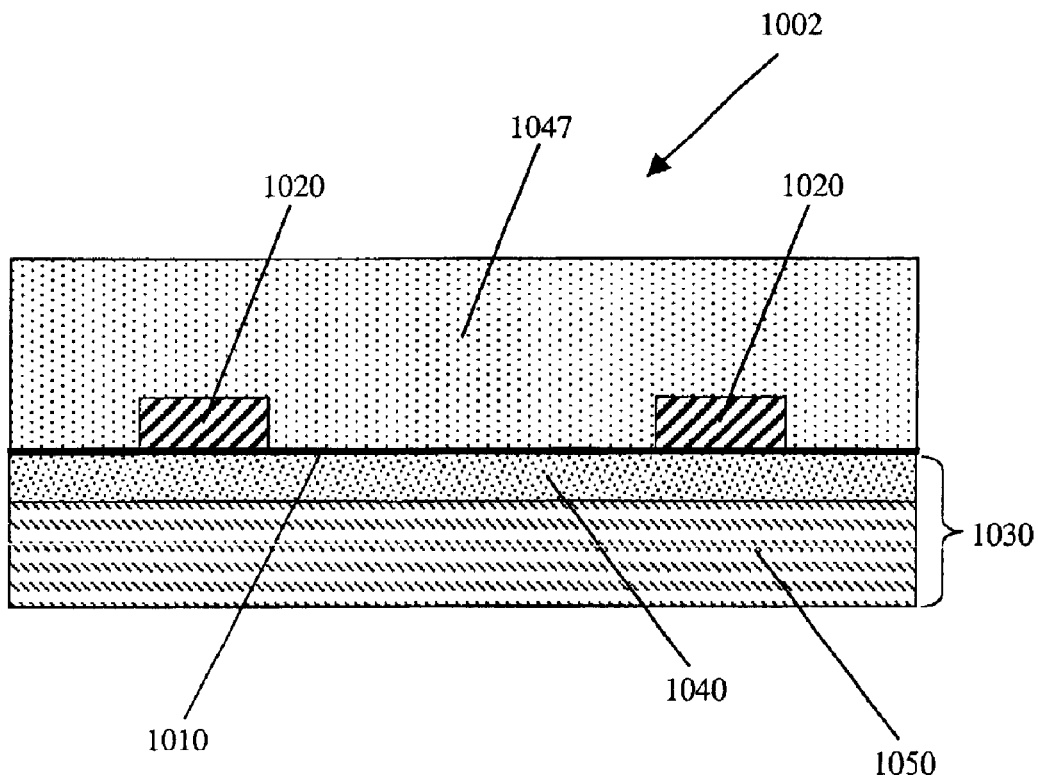
FIG. 10B is a cross section of a nanostructure sensing device with a thicker layer of semipermeable inhibiting material than in FIG. 10A.

FIGS. 10A and 10B illustrate other embodiments of the invention wherein nanostructure sensing devices include a semipermeable inhibiting or passivation material that covers both contact regions and nanostructures.

FIGS. 10A and 10B show, in cross section, a nanostructure sensing devices 1000, 1002 that have a nanostructure 1010 in electrical contact with two conducting elements 1020-1, 1020-2, all over a substrate 1030. The nanostructure 1010 can be any conducting or semiconducting nanostructure known in the art of nanotechnology, as discussed above in reference to FIG. 1. The conducting elements 1020-1, 1020-2 can be made of any conductive material, as has been discussed above in reference to FIG. 1. There can be just two conducting elements 1020-1, 1020-2, as shown, or there can be any number n of conducting elements 1020-1–1020-*n* along the length of the nanostructure 1010. The substrate 1030 can be made of any of a variety of materials consistent with the art of semiconductor manufacturing, as has been discussed above in reference to FIG. 1. The substrate 1030 can contain an insulating or semiconducting layer as a top layer 1040, which is different from an underlying layer 1050. Electrical contact between the nanostructure 1010 and the conducting elements 1020-1, 1020-2 can be direct as shown. Alternatively, there can be intervening conducting layers or other components (not shown) between the nanostructure 1010 and the conducting elements 1020-1, 1020-2. The nanostructure sensing device 1000 in FIG. 10A is covered by a semipermeable inhibiting layer 1045. The inhibiting layer 1045 is at least partially permeable to the analyte of interest.

In environments where cross-sensitivity is of concern, an inhibiting material can be chosen that is substantially permeable to the analyte(s) of interest and substantially impermeable to species that are not of sensing interest. Substantially permeable to the analyte(s) of interest means that the analyte(s) can diffuse through the inhibiting material relatively easily. Substantially impermeable means that species cannot diffuse readily or cannot diffuse at all through the inhibiting material. It can be desirable to exclude species such as moisture, oxygen, ammonia, and nitrous oxide with an inhibiting material layer. Thus an inhibiting layer can be used to tune the selectivity of a nanostructure sensing device.

FIG. 10B shows a nanostructure sensing device 1002 that has a thicker inhibiting layer 1047 than the nanostructure sensing device 1000 in FIG. 10A. For inhibiting layers 1045, 1047 that are semipermeable to an analyte of interest, the thicker the layer, the longer it will take for the analyte to diffuse through the layer to reach and interact with the sensor. For a thick enough inhibiting layer, only a fraction of the analyte can diffuse through to reach the sensor. Thus, the sensitivity of the sensor can be tuned by adjusting the thickness of a semipermeable inhibiting layer. For thin layers, the sensor can respond to relatively low concentrations of the analyte of interest. For thick layers, the sensor can respond only to high concentrations of the analyte.

Materials that can be useful for the inhibiting layer 1045, 1047 include Teflon™, Nafion™, polyethylene and polypropylene. In one arrangement, the thickness of the semipermeable layer 1045, 1047 can be between 3 nm and 500 nm. In another arrangement, the thickness of the semipermeable layer 1045, 1047 can be between 5 nm and 100 nm.

This invention has been described herein in considerable detail to provide those skilled in the art with information relevant to apply the novel principles and to construct and use such specialized components as are required. However, it is to be understood that the invention can be carried out by different materials and structures, and that various modifications can be accomplished without departing from the scope of the invention itself.

We claim:

1. A nanostructure sensing device for detecting an analyte, comprising:
    a substrate;
    a first nanostructure disposed over the substrate;
    a first conductive element disposed over the substrate and forming a first electrical junction with a first nanostructure;
    a second conductive element disposed over the substrate and forming a second electrical junction with the first nanostructure;
    contact regions adjacent to junctions of the conductive elements and the first nanostructure; and
    inhibiting material on at least the contact regions.

2. The nanostructure sensing device of claim 1, further comprising a gate electrode in proximity to the first nanostructure.

3. The nanostructure sensing device of claim 2, wherein the gate electrode is an undifferentiated gate electrode.

4. The nanostructure sensing device of claim 1, further comprising a trench in the substrate below at least a portion of the first nanostructure.

5. The nanostructure sensing device of claim 1, wherein the first nanostructure is selected from the group consisting of nanotubes, nanowires, nanofibers, and nanorods.

6. The nanostructure sensing device of claim 1, wherein the first nanostructure comprises a single-wall carbon nanotube.

7. The nanostructure sensing device of claim 1, wherein the substrate comprises a top layer facing the first nanostructure.

8. The nanostructure sensing device of claim 7, wherein the top layer comprises a material selected from the group consisting of semiconductors, semiconductor oxides, semiconductor nitrides, and combinations thereof.

9. The nanostructure sensing device of claim 7, wherein the top layer comprises a gate dielectric.

10. The nanostructure sensing device of claim 7, wherein the top layer comprises a diffusion barrier to metals.

11. The nanostructure sensing device of claim 1, wherein the conductive elements comprise metal lines in contact with the substrate.

12. The nanostructure sensing device of claim 1, wherein the contact regions comprise Schottky barriers.

13. The nanostructure sensing device of claim 1, wherein the contact region extends at least 5 nm from the junctions of the conductive elements with the first nanostructure along surfaces of the conductive elements and the first nanostructure.

14. The nanostructure sensing device of claim 1, wherein the contact region extends at least 50 nm from the junctions of the conductive elements with the first nanostructure along surfaces of the conductive elements and the first nanostructure.

15. The nanostructure sensing device of claim 1, wherein the contact region extends at least 1 μm from the junctions of the conductive elements with the first nanostructure along surfaces of the conductive elements and the first nanostructure.

16. The nanostructure sensing device of claim 1, wherein the inhibiting material is in direct contact with the contact regions.

17. The nanostructure sensing device of claim 1, wherein the inhibiting material is electrically insulating.

18. The nanostructure sensing device of claim 1, wherein the inhibiting material is impermeable to at least one species.

19. The nanostructure sensing device of claim 1, wherein the inhibiting material is substantially impermeable to water.

20. The nanostructure sensing device of claim 1, wherein the inhibiting material is substantially impermeable to the analyte.

21. The nanostructure sensing device of claim 1, wherein the inhibiting material comprises more than one material layer.

22. The nanostructure sensing device of claim 1, wherein the inhibiting material is selected from the group consisting of silicon oxides, fluorinated, hydrogenated and carbonated silicon oxides, silicon nitride, metal oxides, and combinations thereof.

23. The nanostructure sensing device of claim 1, wherein the inhibiting material covers substantially both the contact regions and at least a portion of the first conducting element.

24. The nanostructure sensing device of claim 1, wherein the at least one nanostructure comprises functionalization for the analyte.

25. The nanostructure sensing device of claim 1, wherein the inhibiting material covers both the contact regions and at least a substantial portion of the first nanostructure.

26. The nanostructure sensing device of claim 25, wherein the inhibiting material is a least partially permeable to the analyte.

27. The nanostructure sensing device of claim 26, wherein the thickness of the inhibiting material is chosen to tune selectivity for the analyte of the nanostructure sensing device.

28. The nanostructure sensing device of claim 26, wherein the thickness of the inhibiting material is chosen to tune sensitivity to the analyte of the nanostructure sensing device.

29. The device of claim 25, wherein the inhibiting material is impermeable to moisture.

30. The device of claim 25, wherein the inhibiting material is impermeable to at least one species selected from the group consisting of oxygen, ammonia, and nitrous oxide.

31. The device of claim 25, wherein the inhibiting material reduces cross sensitivity of the device.

32. The nanostructure sensing device of claim 25, wherein the inhibiting material is selected from the group consisting of Teflon™, Nafion™, polyethylene and polypropylene.

33. The device of claim 25, wherein the inhibiting material has a thickness between about 3 nm and 500 nm.

34. A nanostructure sensing device for detecting at least one analyte, comprising:
    a substrate;
    a first nanostructure disposed over the substrate;
    a first conductive element disposed over the substrate and forming an electrical junction with the first nanostructure;
    a second conductive element disposed over the substrate and forming an electrical junction with the first nanostructure;
    a first metal node in contact with the first nanostructure; and
    contact regions adjacent to junctions of the conductive elements and the first nanostructure and adjacent to contacts between the first metal node and the first nanostructure.

35. The nanostructure sensing device of claim 34, wherein the conductive elements are connected to an electric circuit that includes an electrical supply and a meter.

36. The nanostructure sensing device of claim 34, wherein the metal node is not connected to an electric circuit.

37. The nanostructure sensing device of claim 34, further comprising a gate electrode.

38. An electronic nanostructure device, comprising:

a substrate;

a first nanostructure disposed over the substrate;

a first conductive element disposed over the substrate and forming a first electrical junction with a first nanostructure;

a second conductive element disposed over the substrate and forming a second electrical junction with the first nanostructure;

contact regions adjacent to junctions of the conductive elements and the first nanostructure;

passivation material on the contact regions; and a portion of the first nanostructure substantially free of passivation material.

39. The device of claim 38, further comprising a gate electrode in proximity to the first nanostructure.

* * * * *